(12) United States Patent
Hoffmann et al.

(10) Patent No.: US 8,268,775 B2
(45) Date of Patent: Sep. 18, 2012

(54) MACROLACTONE DERIVATIVES

(75) Inventors: Holger Hoffmann, Frankfurt am Main (DE); Christine Klemke-Jahn, Frankfurt am Main (DE); Dietmar Schummer, Frankfurt am Main (DE); Herbert Kogler, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/640,273

(22) Filed: Dec. 17, 2009

(65) Prior Publication Data
US 2010/0256049 A1 Oct. 7, 2010

Related U.S. Application Data

(63) Continuation of application No. PCT/EP2008/004971, filed on Jun. 20, 2008.

(30) Foreign Application Priority Data

Jul. 4, 2007 (EP) .................................... 07290841

(51) Int. Cl.
*A61K 38/00* (2006.01)
*C09F 1/00* (2006.01)
(52) U.S. Cl. ........................................ 514/3.4; 530/206
(58) Field of Classification Search .................. 514/3.4; 530/206
See application file for complete search history.

(56) References Cited

U.S. PATENT DOCUMENTS
2009/0221520 A1 9/2009 Malpartida Romero et al.

FOREIGN PATENT DOCUMENTS
| WO | WO 01/07439 A2 | 2/2001 |
| WO | WO0107439 A * | 2/2001 |
| WO | WO 2006/100330 A2 | 9/2006 |

OTHER PUBLICATIONS

Medline Plus Fungal Infection, Mycoses, http://www.nlm.nih.gov/medlineplus/fungalinfections.html.*
American Association for Clinical Chemistry; Lab Tests Online, Fungal Infections, http://labtestsonline.org/understanding/conditions/fungal.*
Fungus Infections: Preventing Recurrence; American Osteopathic College of Dermatology, http://www.aocd.org/skin/dermatologic_diseases/fungus_preventing.html.*
Gerth et al, Inexpensive Media for Mass Cultivation of Myxobacteria, Appl. Microbiol. Biotechnol., 1984 (19) pp. 23-28.
Jones et al, Target-Directed Enediynes: Designed Estramycins, J. Org. Chem., 2001 (66) pp. 3686-3695.
Pettus et al, A Fully Synthetic Route to the Neurotrophic Illicinones Syntheses of Tricyciollicinone and Bicycloillicinone Aldehyde, J. Am. Chem. Soc., 2000 (122) pp. 6160-6168.

* cited by examiner

*Primary Examiner* — Christina Bradley
*Assistant Examiner* — Jeanette Lieb
(74) *Attorney, Agent, or Firm* — Scully, Scott, Murphy & Presser, P.C.

(57) ABSTRACT

The disclosure relates to compounds of the formula (I):

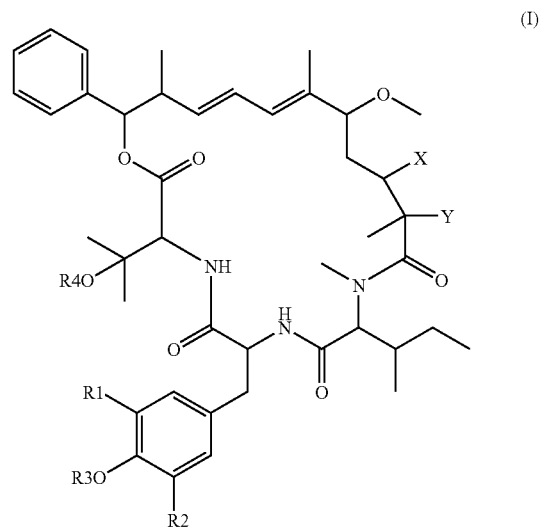

(I)

wherein R1, R2, R3, and R4 are as defined in the disclosure, or a pharmaceutically acceptable salt thereof; which is formed by the microorganism ST 201196 (DSM 18870); the use thereof for the treatment and/or prophylaxis of fungal disorders; medicaments containing a compound of formula (I); processes for production thereof; and the microorganism ST 201196 (DSM 18870).

22 Claims, No Drawings

MACROLACTONE DERIVATIVES

This application is a continuation of International Application No. PCT/EP2008/004971, filed Jun. 20, 2008, which is incorporated herein by reference in its entirety; which claims the benefit of priority of European Patent Application No. 07290841.1, filed Jul. 4, 2007.

The present invention relates to novel macrolactones, and processes for their preparation and use. It has now been found that the microorganism strain ST 201196 (DSM 18870) is able to form novel macrocycles which have a strongly antifungal activity against the fungus *Candida albicans*. The compounds are accordingly suitable for the treatment of local and/or systemic fungal disorders.

A large number of antiinfectives are employed therapeutically for the treatment of infectious diseases. The causative organisms, however, are becoming increasingly resistant to the medicaments used, and a great danger even impends due to "multi-resistant microorganisms", which carry resistances not only against single, but simultaneously against several, anti-infective groups. There are even causative organisms which have become resistant to all anti-infectives obtainable commercially. Infectious diseases which are caused by microorganisms of this type are no longer treatable. There is therefore a great need for novel agents which can be employed against resistant microorganisms. Although many thousands of anti-infectives have been described in the literature, most are too toxic in order to be able to be employed as medicaments.

The present invention relates to a compound of the formula (I),

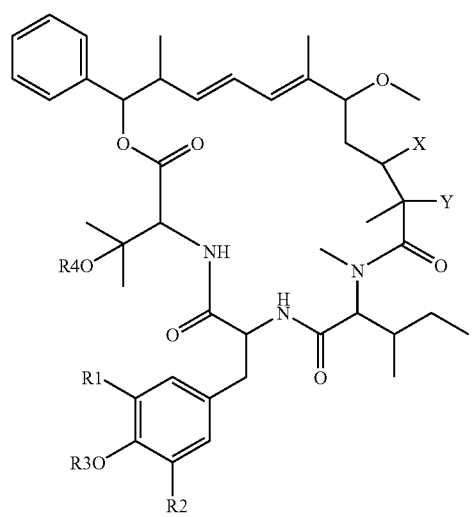

(I)

wherein
X and Y independently of one another are OH, O—(C$_1$-C$_6$)-alkyl, NH$_2$ or
NH—(C$_1$-C$_6$)-alkyl, or X and Y together form a group —O—,
R1 and R2 independently of one another are Cl or H,
R3 is H, (C$_1$-C$_6$)-alkyl, C(=O)—(C$_1$-C$_6$)-alkyl or (C$_1$-C$_6$)-alkylene-NH—(C$_1$-C$_6$)-alkyl, and
R4 is H, (C$_1$-C$_6$)-alkyl or C(=O)—(C$_1$-C$_6$)-alkyl, or a physiologically tolerable salt of a compound of the formula (I).

Preferably, the invention relates to a compound of the formula (I), wherein X and Y together form a group —O—, consequently X and Y in the corresponding preferred compound, together with the C atoms to which they are bonded, form an epoxide group.

More preferably, the invention relates to a compound of the formula (I), wherein R1 and R2 are Cl.

More preferably, the invention relates to a compound of the formula (I), wherein R1 is equal to Cl and R2 is equal to H.

R3 and R4 are preferably independently of one another H, (C$_1$-C$_6$)-alkyl or C(=O)—(C$_1$-C$_6$)-alkyl, particularly preferably both R3 and R4 are equal to H.

Particularly preferably, the invention relates to a compound of the formula (I), wherein X and Y together form a group —O—, R1 and R2 independently of one another are Cl or H, and R3 and R4 independently of one another are H, (C$_1$-C$_6$)-alkyl or C(=O)—(C$_1$-C$_6$)-alkyl, furthermore a compound of the formula (I), wherein X and Y together form a group —O—, R1 and R2 are equal to Cl and R3 and R4 independently of one another are H, (C$_1$-C$_6$)-alkyl or C(=O)—(C$_1$-C$_6$)-alkyl, furthermore a compound of the formula (I), wherein X and Y together form a group —O—, R1 is equal to Cl, R2 is equal to H, and R3 and R4 independently of one another are H, (C$_1$-C$_6$)-alkyl or C(=O)—(C$_1$-C$_6$)-alkyl, furthermore a compound of the formula (I), wherein
X and Y together form a group —O—,
R3 and R4 are equal to H, and
wherein R1 and R2 independently of one another are equal to Cl or H,
preferably wherein R1 and R2 are equal to Cl (also designated as the compound of the formula (II) below),

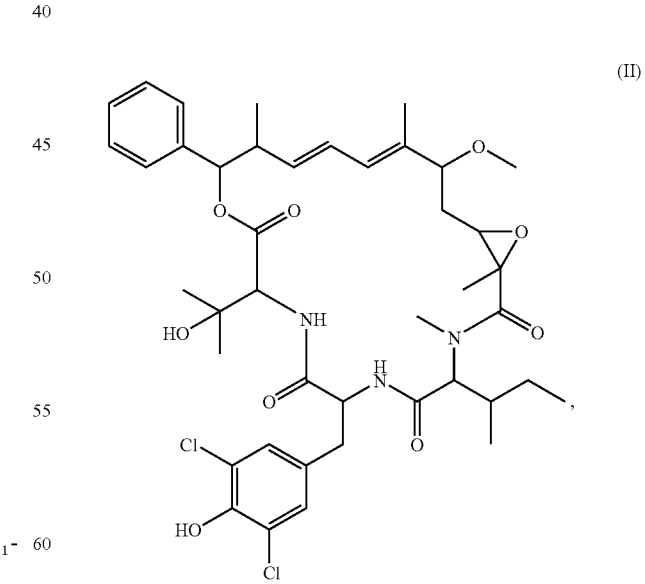

(II)

or wherein more preferably R1 is equal to Cl and R2 is equal to H (also designated as the compound of the formula (III) below),

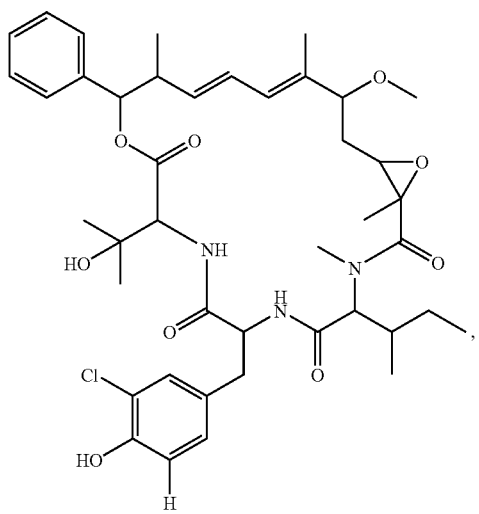

(III)

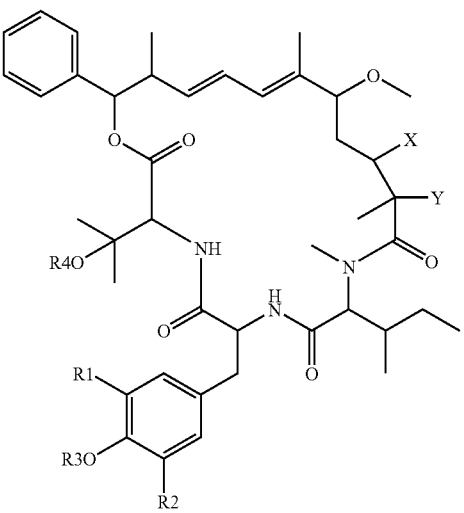

(I)

or wherein more preferably R1 and R2 are equal to H.

$(C_1-C_6)$-Alkyl is a straight-chain or branched alkyl group having 1 to 6 carbon atoms, for example methyl, ethyl, n-propyl, isopropyl, n-butyl, sec-butyl, tert-butyl, n-pentyl or n-hexyl.

Chiral centers in the compounds of the formula (I) can be present, if not stated otherwise, in the R or in the S configuration. The invention relates both to the optically pure compounds and stereoisomer mixtures like enantiomer mixtures and diastereomer mixtures.

Physiologically tolerable salts of compounds of the formula (I) are understood as meaning both their organic and inorganic salts, as are described in Remington's Pharmaceutical Sciences (17th edition, page 1418 (1985)). On account of the physical and chemical stability and the solubility, sodium, potassium, calcium and ammonium salts, inter alia, are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

The present invention furthermore relates to all obvious chemical equivalents of the compounds of the formula (I) according to the invention. Equivalents of this type are compounds which exhibit a slight chemical difference, thus have the same action or are converted to the compounds according to the invention under mild conditions. The equivalents mentioned also include, for example, salts, reduction products, oxidation products, esters, ethers, acetals or amides of the compounds of the formula (I) and equivalents which the person skilled in the art can prepare using standard methods.

The invention furthermore relates to a process for the preparation of a compound of the formula (I), wherein
X and Y independently of one another are OH, O—$(C_1-C_6)$-alkyl, $NH_2$ or
NH—$(C_1-C_6)$-alkyl, or X and Y together form a group —O—,
R1 and R2 independently of one another are Cl or H,
R3 is H, $(C_1-C_6)$-alkyl, C(=O)—$(C_1-C_6)$-alkyl or $(C_1-C_6)$-alkylene-NH—$(C_1-C_6)$-alkyl, and
R4 is H, $(C_1-C_6)$-alkyl or C(=O)—$(C_1-C_6)$-alkyl,
or of a physiologically tolerable salt of a compound of the formula (I),
which comprises
1. fermenting the strain ST 201196 (DSM 18870) or one of its variants and/or mutants under suitable conditions in a culture medium which contains a Cl source, until one or more of the compounds of the formula (I) accumulates in the culture medium and
2. isolating a compound of the formula (I) from the culture medium, and
3. optionally derivatizing the compound of the formula (I) and/or converting it into a physiologically tolerable salt.

The culture medium is a nutrient solution or a solid medium containing at least one carbon and nitrogen source, and the customary inorganic salts.

The Cl source used can be, for example, NaCl or $CaCl_2$. In this case, the strain ST 201196 (DSM 18870) preferably produces compounds of the formula (I), in which both radicals R1 and R2 are equal to Cl or in which R is equal to Cl and R2 is equal to H. Preferably, the invention relates to a process for the preparation of a compound of the formula (I), where R1 and R2 are equal to Cl. Furthermore, the invention preferably relates to a process for the preparation of a compound of the formula (I), where R1 is equal to H, R2 is equal to Cl.

Preferably, the invention relates to a process for the preparation of a compound of the formula (I), wherein X and Y form a group —O—, and furthermore R3 and R4 are as described above or preferably H.

Particularly preferably, the invention relates to a process for the preparation of a compound of the formula (II). More particularly preferably, the invention relates to a process for the preparation of a compound of the formula (III). Furthermore, the invention particularly preferably relates to a process for the preparation of a compound of the formula (I), where R1, R2, R3 and R4 are equal to H.

The process according to the invention can be employed for fermentation on the laboratory scale (milliliter to liter scale) and for the industrial scale (cubic meter scale).

Suitable carbon sources for the fermentation are assimilable carbohydrates and sugar alcohols, such as glucose, lactose, sucrose, or D-mannitol and carbohydrate-containing natural products, such as, for example, malt extract or yeast extract. Suitable nitrogen-containing nutrients are: amino acids; peptides and proteins and their degradation products, for example Probion F (Applied Microbiology and Biotechnology 1984, 19(1), 23-28), casein, peptone or tryptone; meat extracts; yeast extracts; gluten; ground seeds, for example of corn, wheat, beans, soybeans or of the cotton plant; distillation residues from alcohol production; meat meals; yeast extracts; ammonium salts; nitrates. Preferably, the nitrogen source is one or more synthetically or biosynthetically obtained peptides. Inorganic salts are, for example, chlorides, carbonates, sulfates or phosphates of the alkali metals or alkaline earth metals, iron, zinc, cobalt and manganese. Trace elements are, for example, cobalt and manganese.

Suitable conditions for the formation of the substances according to the invention are as follows: The formation of the substances according to the invention preferably proceeds in a culture medium which contains either 0.05 to 5%, preferably 0.1 to 2.5%, of Probion F; 0.02 to 1.0%, preferably 0.05 to 0.5%, of $CaCl_2 \times 2\,H_2O$; 0.02 to 1.5%, preferably 0.05 to 0.7%, of $MgSO_4 \times 7\,H_2O$, and 0.00001% to 0.001% of cyanocobalamin, 1-5% of the adsorber resin XAD-16, or 0.05 to 5%, preferably 0.1 to 2.5%, of oatmeal; 0.2 to 5.0%, preferably 0.1 to 2%, of glycerol; 0.02 to 1.0%, preferably 0.05 to 0.5%, of $CaCl_2$; 0.02 to 1.5%, preferably 0.05 to 0.7%, of $MgSO_4 \times 7\,H_2O$, and 0.00001% to 0.001% of cyanocobalamin. The data in percent are in each case based on the weight of the entire nutrient solution.

The culturing of the microorganism is carried out aerobically, that is, for example, in submerse form with shaking or stirring in shaker flasks or fermenters or on a solid medium, optionally with the introduction of air or oxygen. It can be carried out in a temperature range from approximately 18 to 35° C., preferably at approximately 20 to 32° C., in particular at 27 to 30° C. The pH range should be between 4 and 10, preferably between 6.5 and 9. The microorganism is in general cultured under these conditions over a period of 3 to 18 days, preferably 144 to 216 hours. Advantageously, culturing is carried out in a number of stages, i.e. first one or more precultures is prepared in a liquid nutrient medium, which is then inoculated into the actual production medium, the main culture, for example in the volume ratio 1:10 to 1:100. The preculture is obtained, for example, by inoculating the strain in the form of vegetative cells or fruiting bodies into a nutrient solution and allowing it to grow for approximately 3 to 13 days, preferably 96 to 240 hours. Vegetative cells and/or fruiting bodies can be obtained, for example, by allowing the strain to grow for approximately 3 to 15 days, preferably 7 to 10 days, on a solid or liquid nutrient medium, for example yeast agar.

The isolation or purification of the substances of the formula (I) from the culture medium is carried out according to known methods taking into consideration the chemical, physical and biological properties of the natural substances. HPLC was used for testing the concentration of the respective derivatives in the culture medium or in the individual isolation stages.

For isolation, the culture broth is centrifuged and/or filtered off through a suction filter. The mycelium is lyophilized with the XAD, subsequently the natural substances are extracted from the lyophilizate using an organic solvent, for example methanol or 2-propanol. The organic solvent phase contains the natural substances according to the invention; it is optionally concentrated in vacuo and further purified.

The further purification of one or more compounds according to the invention is carried out by chromatography on suitable materials, preferably, for example, on molecular sieves, on silica gel, alumina, on ion exchangers or on adsorber resins or on reversed phases (RP). With the aid of this chromatography, the natural substance derivatives are separated. The chromatography of the compounds according to the invention is carried out using buffered aqueous solutions or mixtures of aqueous and organic solutions.

Mixtures of aqueous or organic solutions are understood as meaning all organic solvents miscible with water, preferably methanol, 2-propanol and acetonitrile, in a concentration of 0 to 100% of solvent or alternatively all buffered aqueous solutions which are miscible with organic solvents. The buffers to be used are the same as indicated above.

The separation of the compounds according to the invention on the basis of their differing polarity is carried out with the aid of reversed phase chromatography, for example on MCI® (adsorber resin, Mitsubishi, Japan) or Amberlite XAD® (TOSOHAAS), or on another hydrophobic material, such as, for example, on RP-8 or RP-18 phases. Moreover, the separation can be carried out with the aid of normal phase chromatography, for example on silica gel, alumina and the like.

The chromatography of the natural substance derivatives was carried out according to methods known to the person skilled in the art, preferably using buffered, basic or acidified aqueous solutions or mixtures of aqueous solutions with alcohols or other, water-miscible organic solvents. Acetonitrile and/or methanol is preferably used as an organic solvent.

Buffered, basic or acidified aqueous solutions are understood as meaning, for example, water, phosphate buffer, ammonium acetate, ammonium formate, citrate buffer in a concentration of up to 0.5 M, and formic acid, acetic acid, trifluoroacetic acid, ammonia, triethylamine or all commercially available acids and bases known to the person skilled in the art, preferably in a concentration of up to 1%. In the case of buffered aqueous solutions, 0.1% ammonium acetate is particularly preferred.

Chromatography was carried out, for example, using a gradient which began with 100% water and ended with 100% solvent; a linear gradient of 5 to 95% acetonitrile was preferably operated.

Alternatively, gel chromatography or chromatography on hydrophobic phases can also be carried out. Gel chromatography is carried out on polyacrylamide or mixed polymer gels, such as, for example, Biogel-P 2® (Biorad) or Fractogel TSK HW 40® (Merck, Germany). The sequence of the aforementioned chromatographies is reversible.

If the compound of the formula (I) is present as a stereoisomer mixture, the stereoisomers can be separated by means of known methods, for example by separation by means of a chiral column.

The derivatization of the OH groups on the 3,5-dichlorotyrosine amino acid of the compound of the formula (I) [R3 equal to H] to an acyl group [R3 equal to $C(=O)-(C_1-C_6)$-alkyl)] and/or of the OH group on the 3-hydroxyvaline amino acid of the compound of the formula (I) [R4 equal to H] to an acyl group [R4 equal to $C(=O)-(C_1-C_6)$-alkyl)] is carried out according to methods known per se (J. March, Advanced Organic Chemistry, John Wiley & Sons, $4^{th}$ Edition, 1992), for example by reaction with an acid chloride in the presence of a base or with an acid anhydride.

The alkylation of the OH group on the 3,5-dichlorotyrosine amino acid of the compound of the formula (I) [R3 equal to H] with an alkyl group [R3 equal to ($C_1$-$C_6$)-alkyl] and/or the OH group on the 3-hydroxyvaline amino acid of the compound of the formula (I) [R4 equal to H] with an alkyl group [R4 equal to ($C_1$-$C_6$)-alkyl] is carried out by means of methods known per se to the person skilled in the art (J. March, Advanced Organic Chemistry, John Wiley & Sons, $4^{th}$ Edition, 1992), for example by reaction with a ($C_1$-$C_6$)-alkyl bromide in the presence of a base or in the case of a methylation by reaction with methyl iodide or $Me_2SO_4$.

A selective differentiation between the phenolic OH group (R3=H) and the aliphatic OH group (R4=H) is carried out by means of methods known per se to the person skilled in the art for the introduction of protective groups (T. W. Greene, P. G. M. Wuts, Protective Groups in Organic Synthesis, John Wiley & Sons, $3^{rd}$ Edition, 1999). For example, Pettus et al. (J. Am. Chem. Soc. 2000, 122, 6160-6168) describes a selective alkylation of a phenolic OH group in the presence of a tertiary aliphatic alcohol by reaction with ($C_1$-$C_6$)-alkyl bromide in the presence of $K_2CO_3$ in acetone or by reaction with ($C_1$-$C_6$)-alkyl-OH in the presence of $(CF_3CO)_2O$ and $CuCl_2$ hydrate in DBU. A further possibility for differentiation between the phenolic OH group and the aliphatic OH group is carried out by means of the methods known per se to the person skilled in the art for the selective deprotection of a bis-alkylated [R3 equal to R4 equal to ($C_1$-$C_6$)-alkyl] or of a bis-acylated [R3 equal to R4 equal to C(=O)—($C_1$-$C_6$)-alkyl]] compound of the formula (I) (T. W. Greene, P. G. M. Wuts, Protective Groups in Organic Synthesis, John Wiley & Sons, $3^{rd}$ Edition, 1999). For example, Jones et al. (J. Org. Chem. 2001, 66, 3688-3695) describe the selective deprotection of a tert-butylsilyl (TBS)-protected phenol in the presence of a TBS-protected tertiary alcohol by tert-butylammonium fluoride (TBAF) at −20° C. The phenolic OH group (R3=H) can furthermore be derivatized to a group —($C_1$-$C_6$)-alkylene-NH—($C_1$-$C_6$)-alkyl by reaction with $H_2N$—($C_1$-$C_6$)-alkyl in the presence of Cl—[($C_1$-$C_6$)-alkyl]-Cl or Br—[($C_1$-$C_6$)-alkyl]-Br.

The derivatization of compounds of the formula (I), in which X and Y form a group —O— to a compound of the formula (I), in which X and Y independently of one another are OH, O—($C_1$-$C_6$)-alkyl, $NH_2$ or NH—($C_1$-$C_6$)-alkyl, is carried out by means of methods known per se to the person skilled in the art (J. March, Advanced Organic Chemistry, John Wiley & Sons, $4^{th}$ Edition, 1992), for example by reaction of the epoxide group with a ($C_1$-$C_6$)-alcoholate [X equal to OH if Y equal to O—($C_1$-$C_6$)-alkyl, or Y equal to OH if X equal to O—($C_1$-$C_6$)-alkyl], $NH_3$ [X equal to OH if Y equal to $NH_2$, or Y equal to OH if X equal to $NH_2$], or $H_2N$—($C_1$-$C_6$)-alkyl [X equal to OH if Y equal to NH—($C_1$-$C_6$)-alkyl, or Y equal to OH if X equal to NH—($C_1$-$C_6$)-alkyl].

An isolate of the microorganism strain ST 201196 was deposited at the Deutsche Sammlung von Mikroorganismen and Zellkulturen [German Collection of Microorganisms and Cell Cultures] GmbH (DSMZ), Mascheroder Weg 1B, 38124 Brunswick, Germany, according to the rules of the Budapest Convention on the Aug. 12, 2006 under the following number. The following number was assigned as the deposit number: DSM 18870.

The vegetative cells of the strain ST 201196 (DSM 18870) have a characteristic rod shape. On solid nutrient media, ST 201196 (DSM 18870) forms orange-yellow fruiting bodies, which contain round myxospores. The taxonomy of the strain ST 201196 can therefore be described as *Myxobacterium* sp.

Instead of the strain ST 201196 (DSM 18870), it is also possible to employ its mutants and/or variants which synthesize one or more of the compounds according to the invention.

A mutant is a microorganism in which one or more genes of the genome have been modified, where the gene or the genes which are responsible for the ability of the organism to produce the inventive compound remain functional and inheritable.

Mutants of this type can be produced in a manner known per se by physical means, for example irradiation, such as with ultraviolet or X-ray beams, or chemical mutagens, such as, for example, ethyl methanesulfonate (EMS); 2-hydroxy-4-methoxybenzophenone (MOB) or N-methyl-N'-nitro-N-nitrosoguanidine (MNNG), or as described by Brock et al. in "Biology of Microorganisms", Prentice Hall, page 238-247 (1984).

A variant is a phenotype of the microorganism. Microorganisms have the ability to adapt to their environment and therefore show marked physiological flexibility. In the case of phenotypic adaptation, all cells of the microorganism are involved, where the nature of the modification is not genetically conditioned and is reversible under modified conditions (H. Stolp, Microbial ecology: organismus, habitats, activities. Cambridge University Press, Cambridge, GB, page 180, 1988).

Screening for mutants and/or variants which synthesize one or more of the compounds according to the invention is carried out according to the following scheme:
  lyophilization of the fermentation medium;
  extraction of the lyophilizate with an organic solvent;
  extraction of the compound from the culture filtrate using solid phases;
  analysis by means of HPLC, TLC or by testing of the biological activity.

The described fermentation conditions apply for ST 201196 (DSM 18870) and for mutants and/or variants thereof.

For the detection of the antifungal activity of rapidly growing, aerobic causative organisms, the bouillon dilution method (microdilution) according to a procedure of the CLSI (Clinical and Laboratory Standards Institute, M7-A7, Vol. 26, No. 2) is used. The $IC_{50}$ value was determined. This is the concentration of an active substance which is necessary in order to inhibit the growth of the test organism *Candida albicans* by 50%.

The compound of the formula (II) has an $IC_{50}$ value of 0.06 μg/ml against *Candida albicans*. The compound of the formula (IV) has an $IC_{50}$ value of 0.41 μg/ml against *Candida albicans*.

The invention furthermore relates to the use of the compound of the formula (I) or of a physiologically tolerable salt thereof as a medicament in human or veterinary medicine, in particular for the treatment and/or prophylaxis of fungal disorders. Preferably, the invention relates to the use of a compound of the formula (I) or of a physiologically tolerable salt for the treatment of local and/or systemic fungal disorders.

In addition, the present invention relates to a medicament containing at least one compound of the formula (I), where the compound or the compounds of the formula (I) can be administered as such in substance or preferably as a mixture with one or more of the customary pharmacologically suitable vehicles or excipients.

The compounds according to the invention are stable in the solid state and in solutions in the pH range between 2 and 9, in particular 5 and 7, and can thus be incorporated into customary galenical preparations.

The medicaments according to the invention can be administered orally or parenterally, but rectal administration is also possible in principle. Suitable solid or liquid galenical preparation forms are, for example, granules, powders, tablets, coated tablets, (micro)capsules, suppositories, syrups, emulsions, suspensions, aerosols, drops or injectable solutions in ampoule form, and preparations with protracted release of active substance, in whose preparation pharmacologically suitable vehicles or excipients such as disintegrants, binders, coating agents, swelling agents, glidants or lubricants, flavor additives, sweeteners or solubilizers are customarily used, for example magnesium carbonate, titanium dioxide, lactose, mannitol and other sugars, talc, milk protein, gelatine, starch, vitamins, cellulose and its derivatives, animal or vegetable oils, polyethylene glycols and solvents, such as, for example, sterile water, alcohols, glycerol and polyhydric alcohols.

Optionally, the dose units for oral administration can be microencapsulated in order to delay release or to extend it over a longer period, such as, for example, by coating or embedding the active substance in particle form in suitable polymers, waxes or the like.

Preferably, the pharmaceutical preparations are prepared and administered in dose units, where each unit contains as active constituent a certain dose of one or more compounds of the natural substance derivatives according to the invention. In the case of solid dose units such as tablets, capsules and suppositories, this dose can be up to approximately 500 mg, but preferably approximately 0.1 to 200 mg, and in the case of injection solutions in ampoule form up to approximately 200 mg, but preferably approximately 0.5 to 100 mg, per day.

The daily dose to be administered is dependent on the body weight, age, sex and condition of the mammal. Under certain circumstances, however, higher or lower daily doses can also be appropriate. The administration of the daily dose can be carried out both by single administration in the form of an individual dose unit or else in a number of smaller dose units and by multiple administration of subdivided doses at certain intervals.

The medicaments according to the invention are prepared by optionally mixing one or more of the compounds of the formula (I) according to the invention with one or more of the customary vehicles or excipients, and bringing into a suitable administration form.

The following examples are intended to serve for the more detailed illustration of the invention, without restricting the breadth of the invention in any way.

Percentages relate to the weight. Mixing ratios in the case of liquids relate to the volume, if no other particulars have been given.

EXAMPLE 1

Storage of ST 201196 (DSM 18870) at −135° C.

An agar plate (1% fresh baker's yeast; 1% $CaCl_2 \times 2\ H_2O$; 0.477% HEPES (20 mM); 0.00005% cyanocobalamin; 1.8% agar; pH 7.2) was inoculated with the strain ST 201196 (DSM 18870) and incubated for about 7-10 days at 30° C. The cells of this surface culture were scraped from the agar surface using a sterile spatula, suspended in 1 ml of Casitone medium (1% Casitone (Difco); 0.15% $MgSO_4 \times 7H_2O$; pH 7.0) in cryotubes and stored at −135° C.

EXAMPLE 2

Storage of ST 201196 (DSM 18870) at −196° C.

An agar plate (1% fresh baker's yeast; 1% $CaCl_2 \times 2\ H_2O$; 0.477% HEPES (20 mM); 0.00005% cyanocobalamin; 1.8% agar; pH 7.2) was inoculated with the strain ST 201196 (DSM 18870) and incubated for about 7-10 days at 30° C. The cells of this surface culture were scraped from the agar surface using a sterile spatula, suspended in 1 ml of Casitone medium (1% Casitone (Difco); 0.15% $MgSO_4 \times 7H_2O$; pH 7.0) in cryotubes and stored at −196° C.

EXAMPLE 3

Preparation of a Preculture of ST 201196 (DSM 18870) in an Erlenmeyer Flask 100 ml of nutrient solution (1% fresh baker's yeast; 1% $CaCl_2 \times 2\ H_2O$; 0.477% HEPES (20 mM); 0.00005% cyanocobalamin; 1.8% agar; pH 7.2) in a sterile 300 ml Erlenmeyer flask were inoculated with the strain ST 201196 (DSM 18870) and incubated for 7 days at 30° C. and 180 rpm on a rotary shaker. 10 ml (10%) in each case of this preculture were subsequently used for the preparation of the main cultures.

EXAMPLE 4

Preparation of a Liquid Main Culture ST 201196 (DSM 18870) Using Medium 1

A sterile 300 ml Erlenmeyer flask containing 100 ml of the following nutrient solution (1% Probion F; 0.1% $CaCl_2 \times 2\ H_2O$; 0.2% $MgSO_4 \times 7\ H_2O$; 0.00005% cyanocobalamin; 2% of the adsorber resin XAD-16, pH 8.4) was inoculated with 10 ml (10%) of a preculture (see Example 3) or a culture washed on a fresh agar plate (1% fresh baker's yeast; 1% $CaCl_2 \times 2\ H_2O$; 0.477% HEPES (20 mM); 0.00005% cyanocobalamin; 1.8% agar; pH 7.2) and incubated on a shaker at 180 rpm and 30° C. The maximum production of the substances according to the invention was reached after 144 to 216 hours. A 144-196 hour-old submerse culture (inoculum 10%) of the same nutrient solution as described in Example 3 sufficed for the inoculation of 10 to 200 l fermenters.

EXAMPLE 5

Preparation of a Liquid Main Culture ST 201196 (DSM 18870) Using Medium 2

A sterile 300 ml Erlenmeyer flask containing 100 ml of the following nutrient solution (1% oatmeal; 0.5% glycerol; 0.1% $CaCl_2 \times 2\ H_2O$; 0.2% $MgSO_4 \times 7\ H_2O$; 0.00005% cyanocobalamin; 2% of the adsorber resin XAD-16, pH 9.0) was inoculated with 10 ml (10%) of a preculture (see Example 3) or a culture grown on a fresh agar plate (1% fresh baker's yeast; 1% $CaCl_2 \times 2\ H_2O$; 0.477% HEPES (20 mM); 0.00005% cyanocobalamin; 1.8% agar; pH 7.2) and incubated on a shaker at 180 rpm and 30° C. The maximum production of the substances according to the invention was reached after 144 to 216 hours. A 144-196 hour-old submerse culture (inoculum 10%) of the same nutrient solution as described in Example 3 sufficed for the inoculation of 10 to 200 l fermenters.

EXAMPLE 6

Preparation of the Substances according to the Invention in the Fermenter

The 1 l and 50 l fermenters were operated under the following conditions:

| | |
|---|---|
| Inoculum: | 20% |
| Nutrient medium: | 1% oatmeal; 0.5% glycerol; 0.1% yeast extract; 0.1% $CaCl_2 \times 2\ H_2O$; 0.2% $MgSO_4 \times 7\ H_2O$; 0.00005% cyanocobalamin, 2% of the adsorber resin XAD-16 |
| Incubation temperature: | 30° C. |
| Stirrer speed: | 200 rpm |
| Aeration: | 0.6 $m^3/h$ |
| pH regulation: | none, before sterilization pH 7.6 ± 0.3 by means of KOH |
| $pO_2$ regulation: | none |
| Antifoam additive: | 0.05% Desmophen (Bayer) |
| Run time: | 155 h |

The pH regulation was carried out using 10% KOH, or 10% $H_2SO_4$.

EXAMPLE 7

Isolation of the Compounds (II) and (III) from the Shaker Cultures of the Microorganism Strain ST201196 (DSM 18870)

After completion of the fermentation of the microorganism strain ST201196 (DSM 18870), the culture broth from Example 4 (60 l of culture broth) was filtered. The biomass containing the XAD was lyophilized and subsequently extracted with methanol (4×5 l). The methanol extract was reduced to 8 l in vacuo and subsequently applied to a prepared column, which was filled with about 3.0 liters of CHP-20P material (MCI® Gel, 75-150μ, Mitsubishi Chemical Corporation). Elution was carried out using a methanol gradient of from 10% to 95%. The column flow (120 ml/min) was collected in fractions (1 l fractions). Fractions 11 to 14 were combined, the solvent was removed on a Rotavapor and the fraction pool was subsequently lyophilized (yield ~0.9 g).

EXAMPLE 8

Pre-Separation of the Compounds (II) and (III) by RP-18 Chromatography

The fraction pool 11-14 from Example 7 was dissolved in 100 ml of methanol and applied to a Phenomenex Luna® 10μ C18 (2) column (dimensions: 250 mm×50 mm) having a Luna® 10μ C18 (2) pre-column (dimensions: 60 mm×21.2 mm) and eluted over the course of 40 min using a gradient of from 5% to 95% acetonitrile in water (0.1% ammonium acetate, pH 4.6 set using acetic acid). The flow was 190 ml/min, the fraction size 190 ml. Fractions 28-29 and 31 were subsequently worked up further.

EXAMPLE 9

Purification of Compound (II)

Fraction 31 from Example 8 was first lyophilized (yield ~98 mg), subsequently dissolved in 50 ml of methanol and again purified by means of HPLC on a Phenomenex Luna® Axia 5 μm C18 (2) column (dimensions: 100 mm×30 mm) having an XTerra® Prep MS C18 10 μm pre-column (Waters, dimensions: 19×10 mm). Elution was carried out over the course of 40 min using a gradient of from 5% to 95% acetonitrile in water (with addition of 0.1% ammonium acetate, pH 4.6 set using acetic acid). The column flow (50 ml/min) was collected in fractions according to UV. Fractions 4 to 14 contained the compound of the formula (II) and afforded, after lyophilization, 38 mg (purity >95%).

EXAMPLE 10

Characterization of the Compound of the Formula (II)

Colorless solid, crystals from acetonitrile/water
UV: 208, 232, 286 nm
ESI-MS: MW=815.3312
Empirical formula: $C_{42}H_{55}Cl_2N_3O_9$
Specific rotation (MeOH): −0.19°, $\alpha_D$=−38°

TABLE 1

NMR chemical shifts of the macrolactone (II); c = 3 mg/ml in $d_6$-DMSO at 300 K.

| Position | δ ($^{13}C$) | δ ($^1H$) |
|---|---|---|
| 1 | 126.87 | 7.251 |
| 2 (2C) | 127.71 | 7.322 |
| 3 | 125.89 | 7.566 |
| 4 | 139.90 | — |
| 5 | 78.78 | 5.898 |
| 6 | 41.82 | 2.635 |
| 6-Me | 9.50 | 0.961 |
| 7 | 138.29 | 6.175 |
| 8 | 124.58 | 6.379 |
| 9 | 128.83 | 6.116 |
| 10 | 133.27 | — |
| 10-Me | 10.62 | 1.696 |
| 11 | 83.90 | 3.619 |
| 11-OMe | 55.08 | 3.094 |
| 12 | 30.50 | 2.115 |
| | | 1.456 |
| 13 | 57.97 | 2.633 |
| 14 | 61.26 | — |
| 14-Me | 14.81 | 1.427 |
| 15 | 169.23 | — |
| 16 N-Me | 29.59 | 2.979 |
| 17 α | 59.11 | 4.474 |
| β | 30.94 | 1.704 |
| β-Me | 14.14 | 0.348 d |
| γ | 24.15 | 1.218 |
| | | 0.863 |
| δ | 9.99 | 0.770 t |
| 18 CO | 168.59 | — |
| 19 NH | | 8.014 |
| 20 α | 52.67 | 4.686 |
| β | 37.02 | 2.806 |
| | | 2.483 |
| γ | (136.8) | — |
| δ | 129.55 | 7.345 |
| ε | 121.50 | — |
| φ | 147.65 | — |
| φ-OH | | 9.88 br |
| 21 CO | 170.43 | — |
| 22 NH | | 8.596 |
| 23 α | 59.11 | 4.677 |
| β | 71.84 | — |
| β-OH | | 5.110 |
| γ | 24.36 | 1.037 |
| γ' | 28.14 | 1.142 |
| 24 CO | 170.55 | — |

EXAMPLE 11

Purification of Compound (III)

Fractions 28-29 (380 ml) from Example 8 were again purified by means of HPLC on a Waters XTerra® 10 μm C18 column (dimensions: 100 mm×30 mm) having an XTerra® Prep MS C18 10 μm pre-column (Waters, dimensions: 19×10 mm). Elution was carried out over the course of 40 min using a gradient of from 10% to 95% acetonitrile in water (with addition of 10% formic acid, pH=2.0). The column flow (70 ml/min) was collected in fractions according to UV. Fractions 45 to 47 contained the compound of the formula (III) and afforded, after lyophilization, ~5.4 mg (purity >50%).

EXAMPLE 12

Characterization of the Compound (III)

Colorless solid
UV: 204, 232, 286 nm
ESI-MS: MW=799.3002
Empirical formula: $C_{42}H_{56}ClN_3O_9$

TABLE 2

NMR chemical shifts of the macrolactone (III);
c = 5 mg/ml in $d_6$-DMSO at 300 K.

| Position | $\delta$ ($^{13}$C) | $\delta$ ($^1$H) |
|---|---|---|
| 1 | 126.88 | 7.252 |
| 2 (2C) | 127.71 | 7.331 |
| 3 | 125.93 | 7.566 |
| 4 | 139.91 | — |
| 5 | 78.76 | 5.896 |
| 6 | 41.84 | 2.659 br. |
| 6-Me | 9.59 | 0.958 |
| 7 | 138.25 | 6.171 |
| 8 | 124.64 | 6.375 |
| 9 | 128.79 | 6.114 |
| 10 | 133.29 | — |
| 10-Me | 10.68 | 1.692 |
| 11 | 83.86 | 3.620 |
| 11-OMe | 55.09 | 3.090 |
| 12 | 30.52 | 2.113 |
|  |  | 1.470 |
| 13 | 57.98 | 2.642 |
| 14 | 61.23 | — |
| 14-Me | 14.81 | 1.431 |
| 15 | 169.27 | — |
| 16 N-Me | 29.63 | 2.981 |
| 17 α | 59.08 | 4.471 |
| β | 31.04 | 1.693 |
| β-Me | 14.80 | 0.315 d |
| γ | 24.16 | 1.221 |
|  |  | 0.862 |
| δ | 9.99 | 0.773 t |
| 18 CO | 168.57 | — |
| 19 NH |  | 7.995 |
| 20 α | 52.68 | 4.716 |
| β | 37.26 | 2.824 |
|  |  | 2.488 |
| γ | 129.25 | — |
| δ | 129.12 | 7.069 |
| δ' | 130.67 | 7.335 |
| ε | 115.83 | 6.767 |
| ε' | 118.85 | — |
| φ | 151.40 | — |
| φ-OH |  | n.d. |
| 21 CO | 170.73 | — |
| 22 NH |  | 8.636 |
| 23 α | 59.20 | 4.674 |
| β | 71.85 | — |
| β-OH |  | n.d |
| γ | 24.41 | 1.035 |
| γ' | 28.15 | 1.142 |
| 24 CO | 170.54 | — |

EXAMPLE 13

Synthesis of Compound (IV)

Compound (II) (80 mg, 0.098 mmol) was dissolved in 5 ml of acetonitrile and the solution was treated at room temperature with potassium carbonate (27 mg, 0.196 mmol) and methyl iodide (70 mg, 0.490 mmol). The mixture was subsequently stirred for 12 h at 50° C. The solution was filtered and purified by means of HPLC on a Phenomenex Luna® Axia 5 µm C18 (2) column (dimensions: 100 mm×30 mm) having an XTerra® Prep MS C18 10 µm pre-column (Waters, dimensions: 19×10 mm). Elution was carried out over the course of 40 min using a gradient of from 5% to 95% acetonitrile in water (with addition of 0.1% ammonium acetate, pH 4.6, set using acetic acid). The column flow (50 ml/min) was collected in fractions according to UV. Fractions 4 and 5 contained the desired compound of the formula (IV) and afforded, after lyophilization, 50 mg (yield: 61%, purity >95%).

EXAMPLE 14

Characterization of the Compound of the Formula (IV)

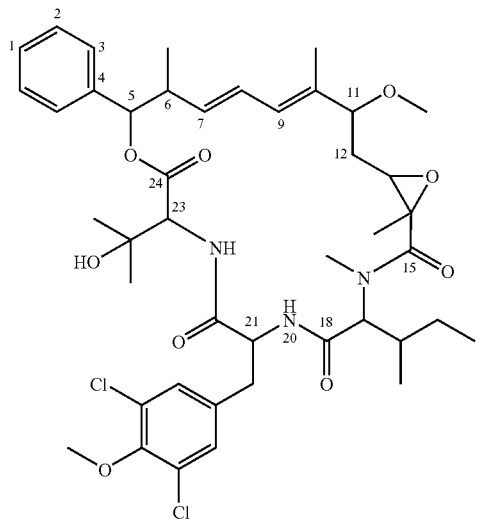

Colorless solid, crystals from acetonitrile/water
UV: 235, 286 nm
MW=830.85
Empirical formula: $C_{43}H_{57}Cl_2N_3O_9$

TABLE 3

NMR chemical shifts of the compound of the formula (IV);
c = 3 mg/ml in $d_6$-DMSO at 300 K.

| Position | $\delta$ ($^{13}$C) | $\delta$ ($^1$H) |
|---|---|---|
| 1 | 126.88 | 7.267 |
| 2 (2C) | 127.72 | 7.332 |
| 3 (2C) | 125.88 | 7.568 |
| 4 | 139.87 | — |
| 5 | 78.78 | 5.903 |
| 6 | 41.81 | 2.660 |
| 6-Me | 9.593 | 0.969 |
| 7 | 138.23 | 6.192 |
| 8 | 124.60 | 6.385 |
| 9 | 128.78 | 6.124 |
| 10 | 133.27 | — |
| 10-Me | 10.65 | 1.700 |
| 11 | 83.88 | 3.624 |
| 11-OMe | 55.08 | 3.103 |
| 12 | 30.46 | 2.130 |

TABLE 3-continued

NMR chemical shifts of the compound of the formula (IV);
c = 3 mg/ml in $d_6$-DMSO at 300 K.

| Position | | $\delta$ ($^{13}$C) | $\delta$ ($^1$H) |
|---|---|---|---|
| | | | 1.470 |
| 13 | | 57.94 | 2.637 |
| 14 | | 61.26 | — |
| 14-Me | | 14.82 | 1.437 |
| 15 | | 169.23 | — |
| 16 N-Me | | 29.55 | 2.984 |
| 17 | α | 59.04 | 4.471 |
| | β | 30.87 | 1.715 |
| | β-Me | 14.20 | 0.284 |
| | γ | 24.10 | 1.216 |
| | | | 0.884 |
| | δ | 9.95 | 0.775 |
| 18 CO | | 168.53 | — |
| 19 NH | | | 8.103 |
| 20 | α | 52.37 | 4.771 |
| | β | 37.19 | 2.889 |
| | | | 2.569 |
| | γ | 136.23 | — |
| | δ | 130.29 | 7.511 |
| | ε | 127.33 | — |
| | φ | 149.79 | — |
| | φ-OMe | 60.29 | 3.742 |
| 21 CO | | 170.19 | — |
| 22 NH | | | 8.620 |
| 23 | α | 59.13 | 4.691 |
| | β | 71.80 | — |
| | β-OH | | 5.161 |
| | γ | 24.38 | 1.047 |
| | γ' | 28.12 | 1.153 |
| 24 CO | | 170.55 | — |

EXAMPLE 15

Synthesis of the Compounds (V) and (VI)

Compound (II) (30 mg, 0.037 mmol) was dissolved in 10 ml of 1,2-dichloroethane and the solution was treated at room temperature with isobutylamine (500 μl, 5.03 mmol). The mixture was stirred for 48 h at 70° C., subsequently filtered and purified by means of HPLC on a Phenomenex Luna® Axia 5 μm C18 (2) column (dimensions: 100 mm×30 mm) having an XTerra® Prep MS C18 10 μm pre-column (Waters, dimensions: 19×10 mm). Elution was carried out over the course of 40 min using a gradient of from 5% to 95% acetonitrile in water (with addition of 0.1% ammonium acetate, pH 4.6 set using acetic acid). The column flow (50 ml/min) was collected in fractions according to UV. Fraction 70 contained the two compounds of the formulae (V) and (VI) and afforded, after lyophilization, 3 mg of the two compounds in a ratio of 55:45.

EXAMPLE 16

Characterization of the Compound of the Formula (V)

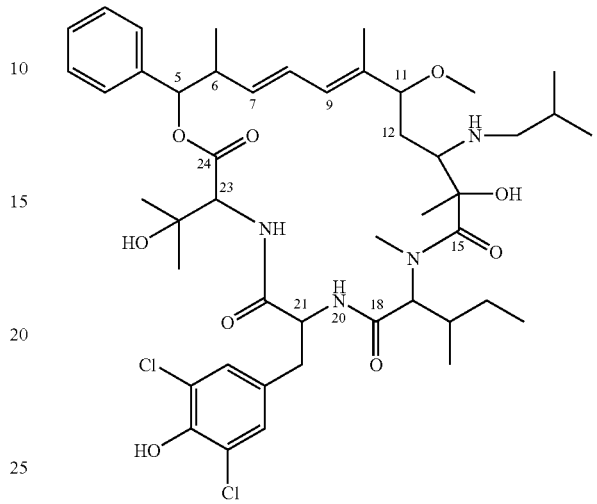

MW=889.97
Empirical formula: $C_{46}H_{66}Cl_2N_4O_9$

TABLE 4

NMR chemical shifts of the compound of the formula (V);
c = 3 mg/ml in $d_6$-DMSO at 300 K.

| Position | | $\delta$ ($^{13}$C) | $\delta$ ($^1$H) |
|---|---|---|---|
| 1 | | 126.94 | 7.244 |
| 2 (2C) | | 127.86 | 7.340 |
| 3 (2C) | | 125.82 | 7.507 |
| 4 | | 139.29 | — |
| 5 | | 78.48 | 5.768 |
| 6 | | 41.63 | 2.679 |
| 6-Me | | 12.06 | 0.880 |
| 7 | | 134.90 | 5.776 |
| 8 | | 126.58 | 6.483 |
| 9 | | 124.04 | 5.901 |
| 10 | | 137.71 | — |
| 10-Me | | 13.72 | 1.690 |
| 11 | | 82.17 | 3.679 |
| 11-OMe | | 55.06 | 3.083 |
| 12 | | 37.38 | 1.379 |
| | | | 1.265 |
| 13 | | 61.04 | 2.927 |
| 13-NH | | | n.d. |
| 13-iBu-1 | | 58.81 | 2.435 |
| | | | 2.460 |
| 13-iBu-2 | | 28.98 | 1.624 |
| 13-iBu-3 | | 20.66 | 0.903 |
| 13-iBu-3 | | 20.66 | 0.896 |
| 14 | | 61.28 | — |
| 14-OH | | | n.d. |
| 14-Me | | 26.44 | 1.302 |
| 15 | | 174.64 | — |
| 16 | | — | — |
| 16 | N-Me | 28.98 | 3.190 |
| 17 | α | 59.71 | 4.750 |
| | β | 32.15 | 1.678 |
| | β-Me | 14.15 | 0.208 |
| | γ | 23.70 | 0.814 |
| | | | 1.207 |
| | δ | 10.17 | 0.724 |
| 18 | CO | 168.46 | — |
| 19 | NH | | 8.242 |

TABLE 4-continued

NMR chemical shifts of the compound of the formula (V); c = 3 mg/ml in $d_6$-DMSO at 300 K.

| Position | | δ ($^{13}$C) | δ ($^1$H) |
|---|---|---|---|
| 20 | α | 52.74 | 4.927 |
| | β | 37.96 | 2.646 |
| | | | 2.843 |
| | γ | 122.4 | — |
| | δ | 129.59 | 7.358 |
| | ε | 121.57 | — |
| | φ | 147.54 | — |
| | φ-OH | | n.d. br. |
| 21 | CO | 170.72 | — |
| 22 | NH | | 8.451 |
| 23 | α | 59.99 | 4.598 |
| | β | 71.16 | — |
| | β-OH | | 5.120 |
| | γ | 25.13 | 1.092 |
| | γ' | 28.09 | 1.191 |
| 24 | CO | 170.72 | — |

EXAMPLE 17

Characterization of the Compound of the Formula (VI)

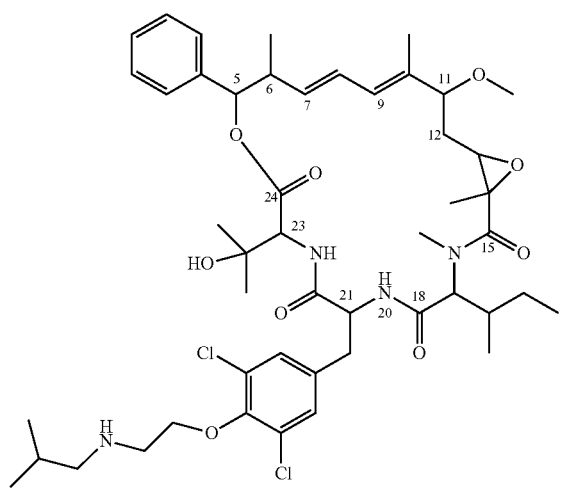

MW=916.00
Empirical formula: $C_{48}H_{68}Cl_2N_4O_9$

TABLE 5

NMR chemical shifts of the compound of the formula (VI); c = 3 mg/ml in $d_6$-DMSO at 300 K.

| Position | | δ ($^{13}$C) | δ ($^1$H) |
|---|---|---|---|
| 1 | | 127.00 | 7.267 |
| 2 (2C) | | 127.72 | 7.330 |
| 3 (2C) | | 125.89 | 7.564 |
| 4 | | 139.88 | — |
| 5 | | 78.79 | 5.900 |
| 6 | | 41.82 | 2.660 |
| 6-Me | | 9.53 | 0.968 |
| 7 | | 138.25 | 6.186 |
| 8 | | 124.61 | 6.383 |
| 9 | | 128.82 | 6.123 |
| 10 | | 133.28 | — |
| 10-Me | | 10.67 | 1.700 |

TABLE 5-continued

NMR chemical shifts of the compound of the formula (VI); c = 3 mg/ml in $d_6$-DMSO at 300 K.

| Position | | δ ($^{13}$C) | δ ($^1$H) |
|---|---|---|---|
| 11 | | 83.89 | 3.626 |
| 11-OMe | | 54.09 | 3.097 |
| 12 | | 30.47 | 2.125 |
| | | | 1.463 |
| 13 | | 57.95 | 2.631 |
| 14 | | 61.27 | — |
| 14-Me | | 14.83 | 1.436 |
| 15 | | 169.25 | — |
| 16 | | — | — |
| 16 | N-Me | 29.36 | 2.979 |
| 17 | α | 59.06 | 4.467 |
| | β | 30.89 | 1.701 |
| | β-Me | 14.26 | 0.274 |
| | γ | 24.13 | 0.864 |
| | | | 1.217 |
| | δ | 9.97 | 0.773 |
| 18 | CO | 168.55 | — |
| 19 | NH | | 8.104 |
| 20 | α | 52.37 | 4.758 |
| | β | 37.10 | 2.555 |
| | | | 2.887 |
| | γ | 136.04 | — |
| | δ | 130.32 | 7.506 |
| | ε | 127.34 | — |
| | φ | 148.96 | — |
| | φ-1 | 72.94 | 3.952 |
| | φ-2 | 48.79 | 2.864 |
| NH | | | n.d. br. |
| iBu-1 | | 57.13 | 2.379 |
| iBu-2 | | 27.94 | 1.662 |
| iBu-3 | | 20.52 | 0.872 |
| iBu-3 | | 20.52 | 0.852 |
| 21 | CO | 170.21 | — |
| 22 | NH | | 8.612 |
| 23 | α | 59.14 | 4.680 |
| | β | 71.81 | — |
| | β-OH | | 5.161 |
| | γ | 24.38 | 1.042 |
| | γ' | 28.13 | 1.149 |
| 24 | CO | 170.56 | — |

EXAMPLE 18

Determination of the Antifungal Activity against *Candida albicans*

A stock solution of 1000 μg/ml of active substance [for example the compound of the formula (II) or the compound of the formula (IV)] in methanol was prepared. The test strain (*Candida albicans* FH 2173) was stored at −80° C. The inoculum was prepared from a fresh, liquid preculture. The preculture was prepared from a bead of the material stored at −80° C. and 30 ml of nutrient medium (Sabourad dextrose broth, Difco) and incubated at 37° C. and 180 revolutions per minute for 24 hours. The inoculum is to be adjusted such that after the inoculation of the test container the necessary number of colony-forming units is achieved. For this, the inoculum was adjusted to a value of $10^7$ CFU/ml (CFU: colony forming units) by means of a photometer at a wavelength of 590 nm. After the adjustment of the inoculum, the suspension was diluted with nutrient solution (Mueller Hinton broth, Difco) 1:100. The microtiter plate was inoculated within 15 minutes of preparation of the inoculum. The exact colony count was determined by means of surface culture. Using the stock solution of the active substance and the nutrient medium (Mueller Hinton broth, Difco), a dilution series was prepared beforehand on the microtiter plate. The active substance was present in a volume of 20 µl and was treated with 20 µl of inoculum such that a total test volume of 40 µl was obtained. The inoculated microtiter plates were subsequently sealed with a lid and incubated at 37° C. in 5% $CO_2$ and 95% atmospheric humidity for 20 hours. For each test, an active substance-free control, a sterile control and, as reference substances, ciprofloxacin and nystatin were co-tested on a 384 well microtiter plate. The microtiter plates were read with the aid of a photometer at a wavelength of 590 nm by measurement of the absorption. The $IC_{50}$ values were subsequently calculated from the values of the dilution series according to a standard process as the concentration of the active substance which is necessary in order to inhibit the growth of the test organism *Candida albicans* by 50%.

What is claimed is:

1. A compound of the formula (I):

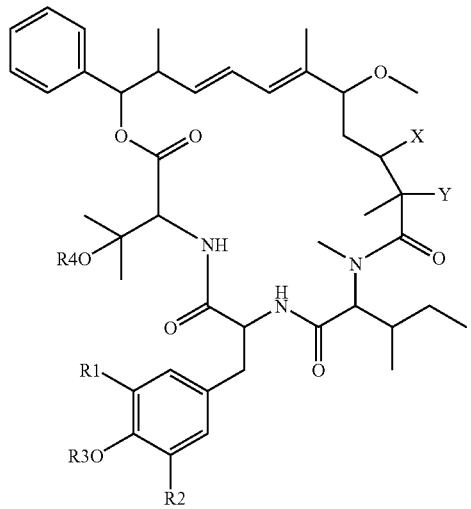

(I)

wherein:
X and Y independently of one another are OH, O—($C_1$-$C_6$)-alkyl, $NH_2$ or NH—($C_1$-$C_6$)-alkyl, or X and Y together form a group —O—;
R1 and R2 independently of one another are Cl or H;
R3 is H, ($C_1$-$C_6$)-alkyl, C(=O)—($C_1$-$C_6$)-alkyl or ($C_1$-$C_6$)-alkylene-NH—($C_1$-$C_6$)-alkyl; and
R4 is H, ($C_1$-$C_6$)-alkyl or C(=O)—($C_1$-$C_6$)-alkyl;
or a physiologically acceptable salt of the compound of the formula (I).

2. The compound of formula (I) according to claim 1, wherein X and Y together form a group —O—.

3. The compound of formula (I) according to claim 1, wherein R3 and R4 independently of one another are H, ($C_1$-$C_6$)-alkyl or C(=O)—($C_1$-$C_6$)-alkyl.

4. The compound of formula (I) according to claim 2, wherein R3 and R4 independently of one another are H, ($C_1$-$C_6$)-alkyl or C(=O)—($C_1$-$C_6$)-alkyl.

5. The compound of formula (I) according to claim 1, wherein R1 and R2 are equal to Cl.

6. The compound of formula (I) according to claim 2, wherein R1 and R2 are equal to Cl.

7. The compound of formula (I) according to claim 3, wherein R1 and R2 are equal to Cl.

8. The compound of formula (I) according to claim 4, wherein R1 and R2 are equal to Cl.

9. The compound of formula (I) according to claim 1, where R1 is equal to Cl and R2 is equal to H.

10. The compound of formula (I) according to claim 2, where R1 is equal to Cl and R2 is equal to H.

11. The compound of formula (I) according to claim 3, where R1 is equal to Cl and R2 is equal to H.

12. The compound of formula (I) according to claim 4, where R1 is equal to Cl and R2 is equal to H.

13. The compound of the formula (I) according to claim 1, wherein R3 and R4 are equal to H.

14. The compound of the formula (I) according to claim 2, wherein R3 and R4 are equal to H.

15. The compound of the formula (I) according to claim 1, where R1, R2, R3 and R4 are equal to H.

16. The compound of the formula (I) according to claim 2, where R1, R2, R3 and R4 are equal to H.

17. A medicament comprising a compound of formula (I) according to claim 1, or a physiologically acceptable salt thereof, and one or more pharmacologically suitable excipients.

18. A method for the treatment of a fungal disorder, comprising administering to a patient in need thereof an effective amount of a compound of formula (1) according to claim 1, or a physiologically acceptable salt thereof.

19. A process for the preparation of a compound of the formula (I),

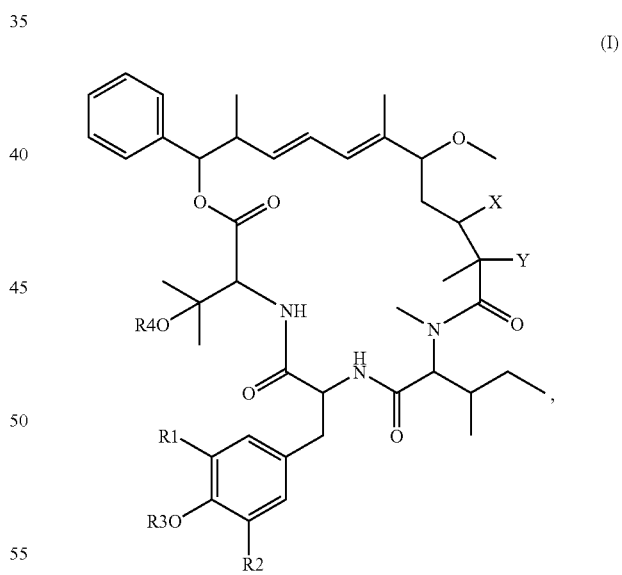

(I)

wherein:
X and Y independently of one another are OH, O—($C_1$-$C_6$)-alkyl, $NH_2$ or NH—($C_1$-$C_6$)-alkyl, or X and Y together form a group —O—;
R1 and R2 independently of one another are Cl or H;
R3 is H, ($C_1$-$C_6$)-alkyl, C(=O)—($C_1$-$C_6$)-alkyl or ($C_1$-$C_6$)-alkylene-NH—($C_1$-$C_6$)-alkyl; and
R4 is H, ($C_1$-$C_6$)-alkyl or C(=O)—($C_1$-$C_6$)-alkyl;

or a physiologically acceptable salt of the compound of the formula (I), comprising:

1) fermenting the strain ST 201196 (DSM 18870) or one of its variants and/or mutants under suitable conditions in a culture medium which contains a Cl source, until one or more of the compounds of formula (I) accumulates in the culture medium; and 2) isolating the compound of formula (I) from the culture medium; and 3) optionally derivatizing the compound of the formula (I) and/or converting it into a physiologically acceptable salt.

20. The process as claimed in claim 19, where in the compound of formula (I), X and Y together form a group —O—, R1 and R2 independently of one another are Cl or H, and R3 and R4 independently of one another are H, $(C_1$-$C_6)$-alkyl or $C(=O)$—$(C_1$-$C_6)$-alkyl.

21. The microorganism strain ST 201196 (DSM 18870).

22. The compound of claim 1 selected from the Formulae II, III, IV, V, and VI:

Formula (II)

Formula (III)

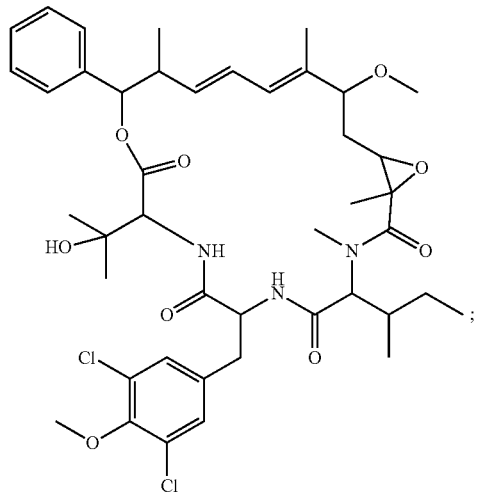

Formula (IV)

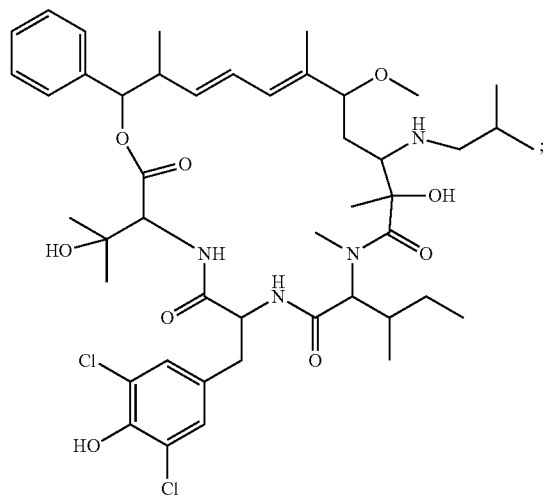

Formula (V)

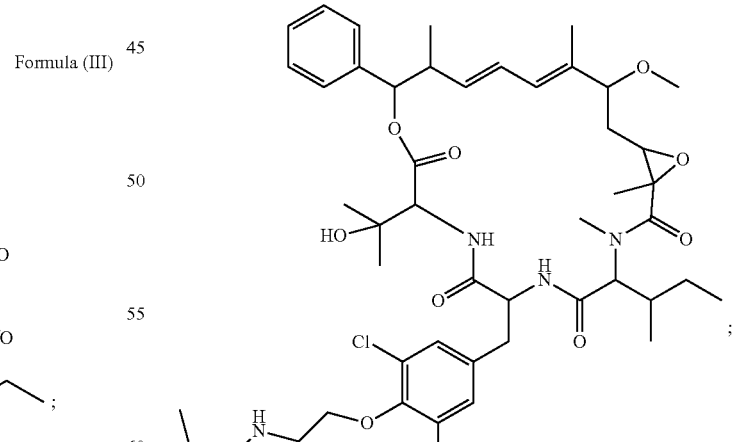

Formula (VI)

or a physiologically tolerable salt of the compound of Formulae (II), (III), (IV), (V).

* * * * *